United States Patent
Lutz

(10) Patent No.: US 8,440,437 B2
(45) Date of Patent: *May 14, 2013

(54) COMBINED INSTALLATION FOR THE PRODUCTION OF BIOGAS AND COMPOST, AND METHOD OF SWITCHING A FERMENTER IN A LIKE INSTALLATION BETWEEN BIOGAS PRODUCTION AND COMPOSTING

(75) Inventor: Peter Lutz, München (DE)

(73) Assignee: Bekon Energy Technologies GmbH & Co., KG, Unterfohring (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/408,573

(22) Filed: Mar. 20, 2009

(65) Prior Publication Data

US 2009/0239209 A1     Sep. 24, 2009

(30) Foreign Application Priority Data

Mar. 20, 2008   (DE) .................. 10 2008 015 240

(51) Int. Cl.
*C12P 5/00*   (2006.01)
*C12M 1/36*   (2006.01)
*C12M 1/34*   (2006.01)
*C12M 1/107*   (2006.01)

(52) U.S. Cl.
USPC ............. 435/166; 435/286.5; 435/289.1; 435/290.1; 435/300.1; 210/104; 210/767

(58) Field of Classification Search .......... 435/166, 435/286.5, 289.1, 290.1, 300.1; 210/104, 210/767

See application file for complete search history.

(56) References Cited

U.S. PATENT DOCUMENTS 5,248,423 A     9/1993   Moletta et al.
6,969,562 B2 *  11/2005  Su et al. .................... 429/410

(Continued)

FOREIGN PATENT DOCUMENTS

DE   34 38 057 A1    4/1986
DE   197 19 323 A1   11/1998

(Continued)

OTHER PUBLICATIONS

Translation of WO 02/06439, Jan. 24, 2002.*

(Continued)

*Primary Examiner* — Nathan Bowers
*Assistant Examiner* — Gautam Prakash
(74) *Attorney, Agent, or Firm* — Morrison & Foerster LLP

(57) ABSTRACT

A combined installation is disclosed for the production of biogas and compost, including a dry fermentation fermenter for producing biogas in a batch mode, a biogas outlet, a purging gas inlet, a biogas line connected to the biogas outlet, a waste gas line, a waste gas chimney connected to the biogas outlet via a first biogas/waste gas line, a waste gas flare connected to the biogas outlet via a second biogas/waste gas line, a fresh air line connected to the purging gas inlet, a control means for connecting the biogas outlet to the biogas line or the biogas/waste gas chimney via the first biogas/waste gas line or the waste gas flare via the second biogas/waste gas line and for connecting the purging gas inlet to the waste gas line or the fresh air line, and a measurement means connected to the control means for detecting methane and carbon dioxide concentrations.

20 Claims, 17 Drawing Sheets

U.S. PATENT DOCUMENTS

| | | | |
|---|---|---|---|
| 7,481,940 B2 * | 1/2009 | Clifford et al. | ............... 210/739 |
| 8,105,823 B2 | 1/2012 | Lutz | |
| 8,187,869 B2 | 5/2012 | Lutz | |
| 2006/0111575 A1 | 5/2006 | DeCourcy et al. | |
| 2006/0223154 A1 * | 10/2006 | Kohr | ............................ 435/166 |
| 2008/0299634 A1 | 12/2008 | Lutz | |
| 2010/0311141 A1 | 12/2010 | Lutz | |

FOREIGN PATENT DOCUMENTS

| | | |
|---|---|---|
| DE | 203 19 847 U1 | 6/2005 |
| EP | 1 301 583 B2 | 2/1989 |
| EP | 0 934 998 A2 | 8/1999 |
| EP | 1 354 940 * | 10/2003 |
| EP | 1 681 274 A2 | 7/2006 |
| EP | 1 762 607 A1 | 3/2007 |
| EP | 1 997 875 A1 | 12/2008 |
| JP | 06-086996 A | 3/1994 |
| RU | 2 254 700 C1 | 6/2005 |
| SU | 1748693 A1 | 7/1992 |
| WO | WO-02/06439 A2 | 1/2002 |

OTHER PUBLICATIONS

Eurasian Search Report mailed Jul. 1, 2009, for EA Application No. 2420-158974, two pages.

Search Report for Eurasian Patent Application No. 200801217, dated Oct. 13, 2008.

Notification of Reason(s) for Refusal mailed Apr. 3, 2012, for JP Application No. 2008-133753, with English Translation, five pages.

Chinese First Office Action mailed Dec. 5, 2012, for CN Patent Application No. 200910128960.5, with English Translation, 20 pages.

* cited by examiner

COMBINED INSTALLATION FOR THE PRODUCTION OF BIOGAS AND COMPOST, AND METHOD OF SWITCHING A FERMENTER IN A LIKE INSTALLATION BETWEEN BIOGAS PRODUCTION AND COMPOSTING

BACKGROUND OF THE INVENTION

The invention relates to a combined installation for the production of biogas and compost from biomass, including at least one fermenter according to the principle of dry fermentation and to a method of switching a fermenter in a like installation between biogas production and composting.

So-called "dry fermentation" allows pourable biomasses from agriculture, from biological waste and from communal cultivated areas to be converted to methane without having to convert the materials to a liquid substrate which can be pumped. Biomasses having a dry substance content of up to 50% can be fermented. This dry fermentation method is described, for example, in EP 0 934 998.

In the case of "dry" fermentation, the material to be fermented is not stirred into a liquid phase as is the case, for example, with liquid fermentation of organic waste. Instead, the fermentation substrate which has been introduced into the fermenter is kept moist all the time by drawing off the percolate at the bottom of the fermenter and spraying it over the biomass again. This results in optimum living conditions for the bacteria. During recirculation of the percolate, the temperature can moreover be regulated, and it is possible to add additives for process optimisation.

From WO 02/06439 a bioreactor or fermenter having the form of a prefabricated garage is known, which is operated according to the principle of dry fermentation in the so-called batch process. In this case, after seeding with already fermented material, the fermenter is filled with the fermentation substrate by means of tractor shovels. The fermentation container is constructed in the form of a garage and is closed by a gastight door. The biomass is fermented with air being excluded, with no further thorough mixing being performed during the process, and with no additional material being supplied. The percolate which seeps out of the material being fermented is drawn off via a drainage groove, is temporarily stored in a tank, and is again sprayed over the fermentation substrate, in order to moisturize it. The fermentation process takes place in the mesophilic temperature range between 34 and 37° C., with temperature equalisation being carried out with the aid of floor heating and wall heating.

The resultant biogas can be used to obtain electricity and heat in a block-type thermal power station (BHKW; Blockheizkraftwerk). In order to ensure that sufficient biogas is always available for the block-type thermal power station, a plurality of fermentation containers are operated with offset timings in the dry fermentation installation. At the end of the dwell time, the fermenter area is emptied completely and then refilled. The fermented substrate is subsequently supplied to composting, resulting in the production of an organic fertiliser that is comparable to conventional composts.

Such fermenters for the production of biogas according to the principle of dry fermentation are further known from DE 203 19 847 U1 and from EP 1 681 274 A2. From DE 34 38 057 it is known to produce compost from the used or fermented biomass from a biogas installation.

Batch operation makes it necessary to shut down the individual fermenters from time to time, i.e., after the biomass present in the fermenter was subjected to complete anaerobic conversion; in other words, the biogas production must be stopped, the fermented biomass must be removed from the respective fermenter, fresh biomass must be charged into the fermenter, and the biogas production has to be resumed. This involves the drawback that it is necessary, for safety reasons, to prevent an explosive biogas/air mixture from being created while the individual fermenters are being loaded and unloaded.

To this end, it is known from EP 1301583 B to flood a fermenter during its operation with waste gas containing carbon dioxide from the block-type thermal power station that is being operated with biogas, in the event of an explosion risk, that is to say if air has entered the fermenter. Subsequently the fermented biomass may be removed without any risk from the fermenter and supplied to a composting installation.

It is therefore the object of the present invention to further develop a biogas installation as known from EP 1301583 B in such as way that post-composting of the spent biomass is simplified.

This object is achieved through the features disclosed herein.

Due to the fact that the spent biomass is composted in the fermenter by switching over from anaerobic fermentation to aerobic composting, it is no longer necessary to convert the spent biomass in a separate composter. A combined installation includes the necessary components in order to enable safe switching, shutting down and unloading, as well as a safe start-up of a fermenter. The fermenter of the invention is configured such that the entire fermentation process, which consists of anaerobic fermentation and aerobic composting, may unfold inside it before it becomes necessary to remove the spent biomass and again charge the fermenter with fresh biomass.

In accordance with a preferred aspect of the invention, a first purging gas inlet opens into the fermenter in the area above the biomass.

In accordance with a preferred aspect of the invention, the fermenter comprises a floor plate having provided therein purging gas passages that are connected to a second purging gas inlet.

In accordance with a preferred aspect of the invention, the purging gas passages are configured for discharging seepage liquids seeping from the biomass during the production of biogas.

Biogas production and processing are maintained for as long as possible even while the fermentation process is terminated by purging with waste gas containing carbon dioxide, i.e., the biogas/waste gas mixture of the fermenter continues to be supplied to the biogas consumer until the quality of this mixture drops below a predetermined degree, before the fermenter is then switched over for composting of the fermented biomass contained in it. Only when the methane concentration in the biogas outlet drops below an upper limit, the biogas line leading to the biogas consumer is disconnected from the biogas outlet. After this, the biogas/waste gas mixture containing only a small quantity of methane is discharged via a waste gas chimney. This is carried out until the methane concentration has dropped to a lower limit at which virtually no methane is contained in the biogas/waste gas mixture any more. Afterwards the fermenter is purged not with waste gas containing carbon dioxide but with fresh air, and discharging the waste gas/biogas/fresh air mixture via the waste gas chimney is continued until the carbon dioxide concentration in the waste gas/biogas/fresh air mixture has dropped to a first limit. Only then the fermenter is switched over for composting. After termination of the composting process, the fermenter may be opened in order to unload the spent biomass and again charge the fermenter with fresh biomass. As a result of composting following fermentation, it is possible to open the fermenter for its unloading and reloading in the absence of any risk.

In accordance with a preferred aspect of the invention, the biogas/waste gas mixture is not emitted to the environment via the waste gas chimney when the upper limit of the methane concentration is reached, but is fed to a waste gas flare and burnt there. Optionally the waste gas flare may be supplied with additional fuel, so that combustion will take place in any case. Combustion of the biogas/waste gas mixture is performed until the methane concentration in the biogas/waste gas mixture becomes less than a medium limit that is situated between the upper and lower limits.

In accordance with preferred aspects of the invention, the composting process is controlled by adjusting the quantity and/or the temperature of the fresh air supplied via the fresh air line, to thus obtain an optimal process medium.

In accordance with a preferred aspect of the invention, the gas mixtures discharged from the fermenter are filtered. As a result of filtering, substances possibly detrimental to the consumers, which might result in clogging of valves, for instance, are removed to the largest possible extent.

In accordance with a preferred aspect of the invention, an explosive biogas/air mixture is safely prevented from being formed during start-up.

This fermenter which has been started again is connected to the biogas line at a fourth methane concentration limit, which is equal to the upper limit.

The waste gas for purging the fermenter is provided, for example, by an internal combustion engine.

In accordance with a preferred embodiment of the invention, the waste gas containing carbon dioxide is provided from a biogas processing means disposed downstream of the at least one fermenter.

Advantageous aspects of the invention are disclosed herein.

Further details, features and advantages of the invention will become evident from the following description of exemplary embodiments with reference to the drawings, in which:

DESCRIPTION OF EMBODIMENTS

Figure 1:
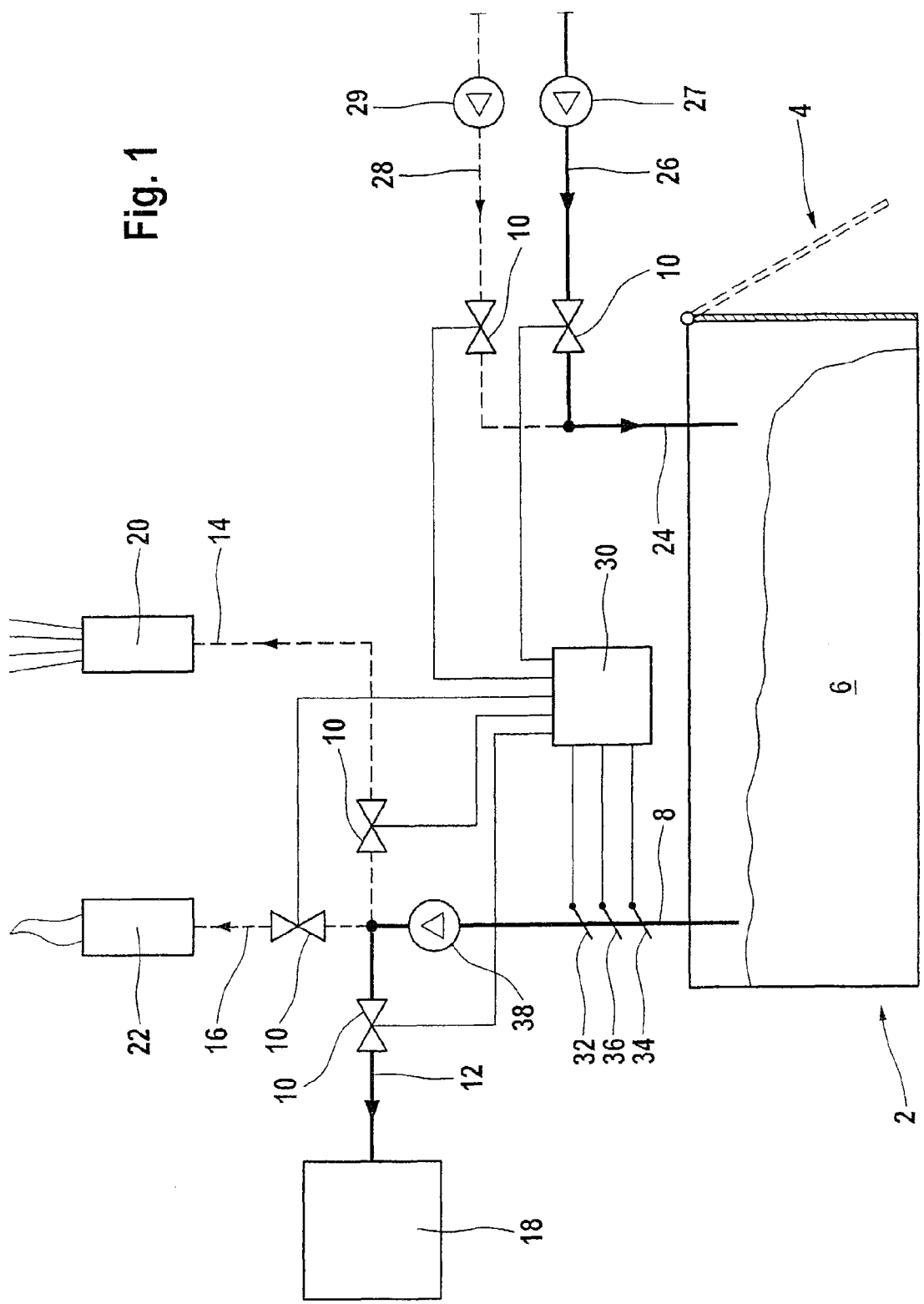
FIGS. 1 to 7 show schematic representations of various operating states during termination of the fermentation process in a fermenter of a combined installation and during (re-)starting of the fermenter in accordance with a first embodiment of the invention.

FIGS. 1 to 7 show a first embodiment of a combined installation according to the present invention including a single fermenter 2. The fermenter 2 has a cuboid shape and is constructed approximately in the form of a prefabricated garage. The fermenter 2 can be filled with biomass 6 and emptied again by means of a tractor shovel through a loading and unloading opening 4 which extends over one of the end faces of the cuboid fermenter 2. Reference is made to WO 02/06439 with regard to details of the construction of the fermenter 2.

The fermenter 2 further includes a biogas outlet 8 adapted to be connected via valves 10 to a biogas line 12, a first biogas/waste gas line 14 and a second biogas/waste gas line 16. The biogas line 12 leads to a block-type thermal power station 18 constituting a biogas-utilising means. The first biogas/waste gas line 14 leads to a biogas/waste gas chimney 20. The second biogas/waste gas line 16 leads to a waste gas flare 22. Furthermore, the fermenter 2 includes a purging gas inlet 24 adapted to be connected via valves 10 to a waste gas line 26 or to a fresh air line 28. A waste gas fan 27 is arranged in the waste gas line 26 and may be used to pump waste gas into the fermenter 2. A fresh air fan 29 for sucking in fresh air from the environment is arranged in the fresh air line 28. Waste gas containing carbon dioxide is passed into the fermenter 2 as purging gas via the waste gas line 26, and fresh air is passed into the fermenter 2 via the fresh air line 28.

The valves 10 are connected to a control means 30 and are opened or closed by means of the control means 30. The control means 30 is also connected to a first measurement sensor 32 which is arranged in the biogas outlet 8 and detects the methane concentration in the respective gas mixture. The control means 30 is furthermore connected to a second measurement sensor 34 which is likewise arranged in the biogas outlet 8 and detects the carbon dioxide concentration in the respective gas mixture. The control means 30 is also connected to a third measurement sensor 36 which is arranged in the biogas outlet 8 and detects the gas volume flow in the biogas outlet. Optionally the extraction of gas from the fermenter 2 can be assisted by a fan 38 which is arranged in the biogas outlet.

FIGS. 1 to 7 show various phases of terminating the fermentation process inside the fermenter 2 and starting the fermenter 2, with active lines and positions of components being illustrated by solid lines, while lines and positions of components which are inactive or shut off, respectively, are illustrated by dashed lines. In accordance with the invention, aerobic conversion of the fermented biomass follows immediately after the fermentation process in the same fermenter by suitably switching the latter over to composting before the fermenter is then opened, unloaded, reloaded and started up again.

FIG. 1 shows the first phase of terminating the fermentation process inside the fermenter 2, in which waste gas containing carbon dioxide is pumped into the interior of the fermenter 2 via the waste gas line 26 and the purging gas inlet 24. The biogas outlet 8 is still connected to the biogas line 12, so that the biogas/waste gas mixture continues to be passed on to the block-type thermal power station 18.

Figure 2:
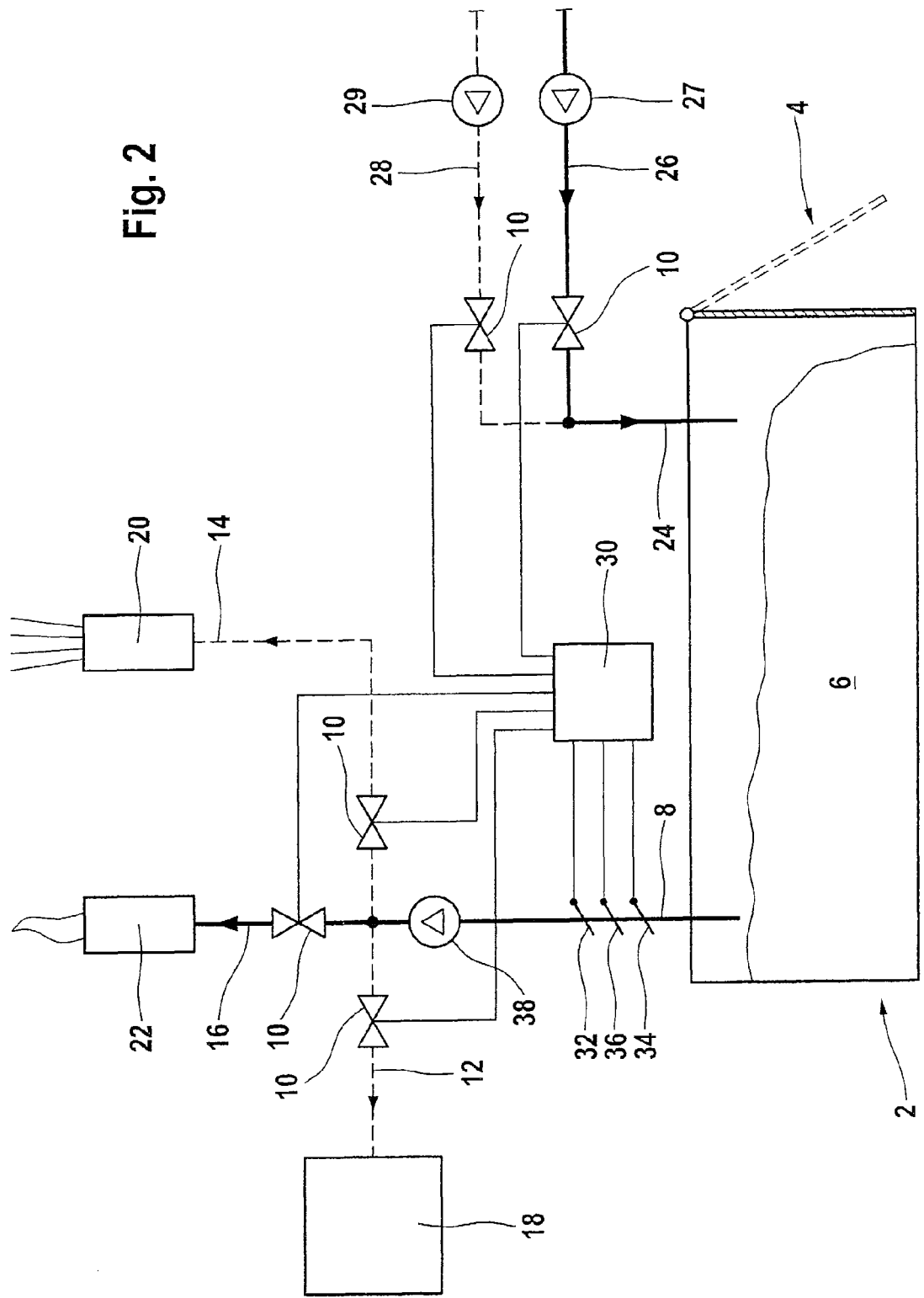

Only when the methane concentration detected by the first measurement sensor 32 in the biogas outlet 8 has dropped below an upper limit, the valve 10 in the biogas line 12 is closed by the control means 30 and the valve 10 in the second biogas/waste gas line 16 is opened in a second phase, as is illustrated in FIG. 2. In this second phase of terminating the fermentation process in the fermenter 2, the biogas/waste gas mixture is burnt in the waste gas flare 22. Optionally this combustion process can be assisted by adding additional fuel.

Figure 3:
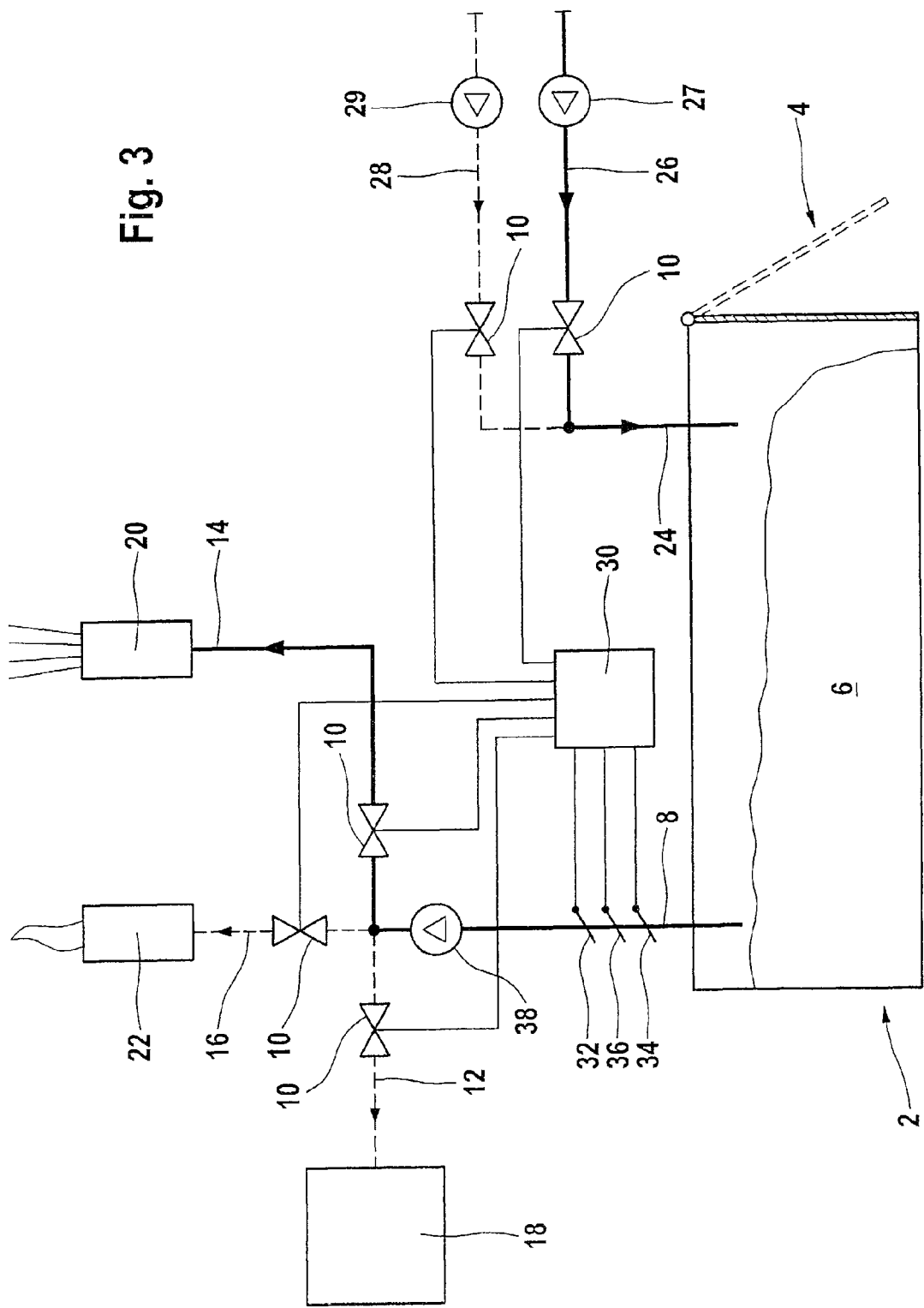

When the methane concentration detected by the first measurement sensor 32 in the biogas outlet 8 has dropped below a medium limit, the valve 10 in the second biogas/waste gas line 16 is closed by the control means 30 and the valve 10 in the first biogas/waste gas line 14 is opened in a third phase, as is illustrated in FIG. 3. In this third phase of terminating the fermentation process inside the fermenter 2, the biogas/waste gas mixture is emitted to the environment via the waste gas chimney 20.

Figure 4:
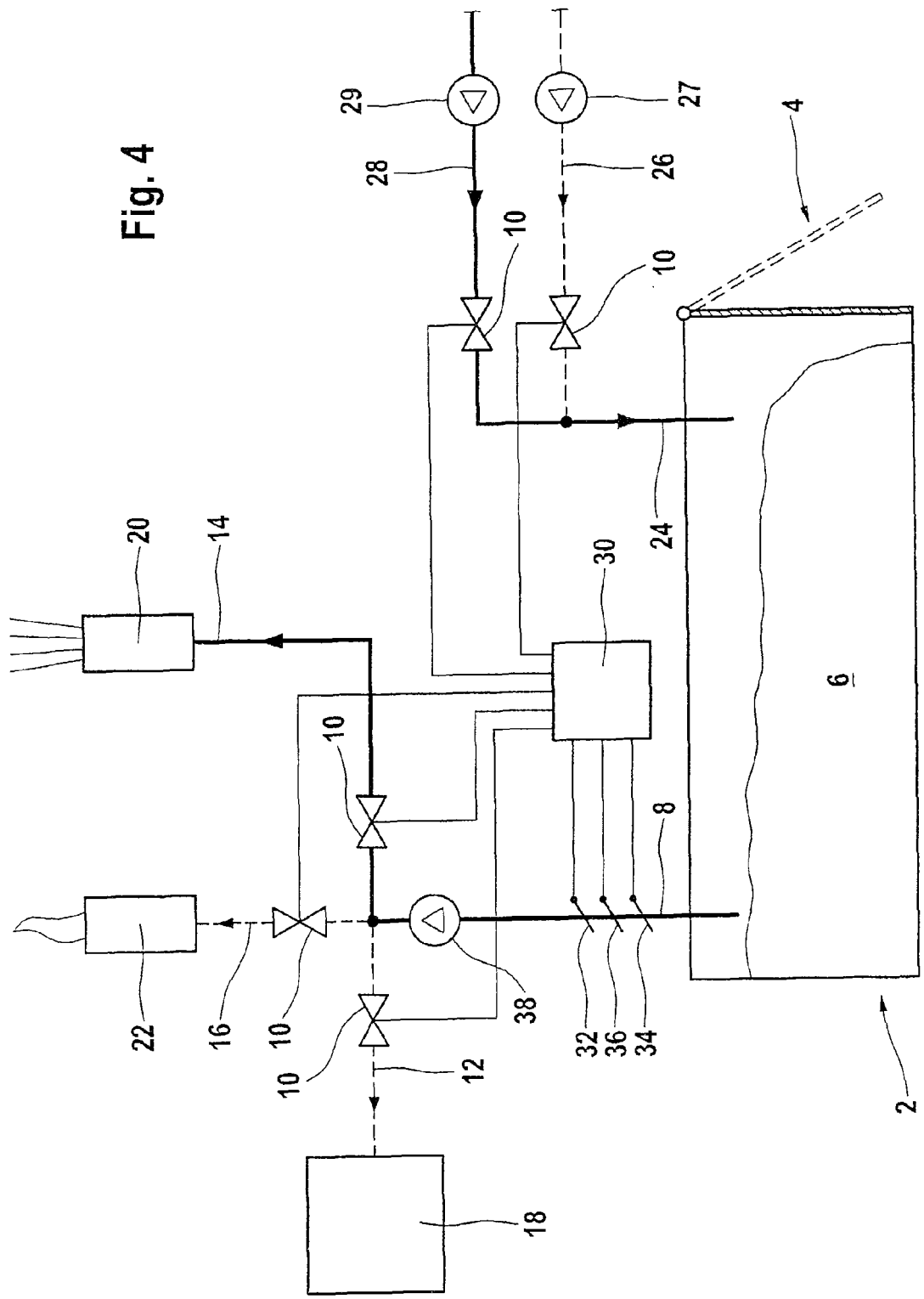

When the methane concentration detected by the first measurement sensor 32 in the biogas outlet 8 has dropped below a lower limit, the valve 10 in the waste gas line 26 is closed and the valve 10 in the fresh air line 28 is opened in a fourth phase, as is illustrated in FIG. 4. In this fourth phase of terminating the fermentation process inside the fermenter 2, fresh air is pumped into the fermenter 2 via the fresh air line 28 and the purging gas inlet 24. The waste gas/air mixture continues to be emitted to the environment via the biogas outlet 8 and the first biogas/waste gas line 14 in the waste gas chimney 20.

Figure 5:
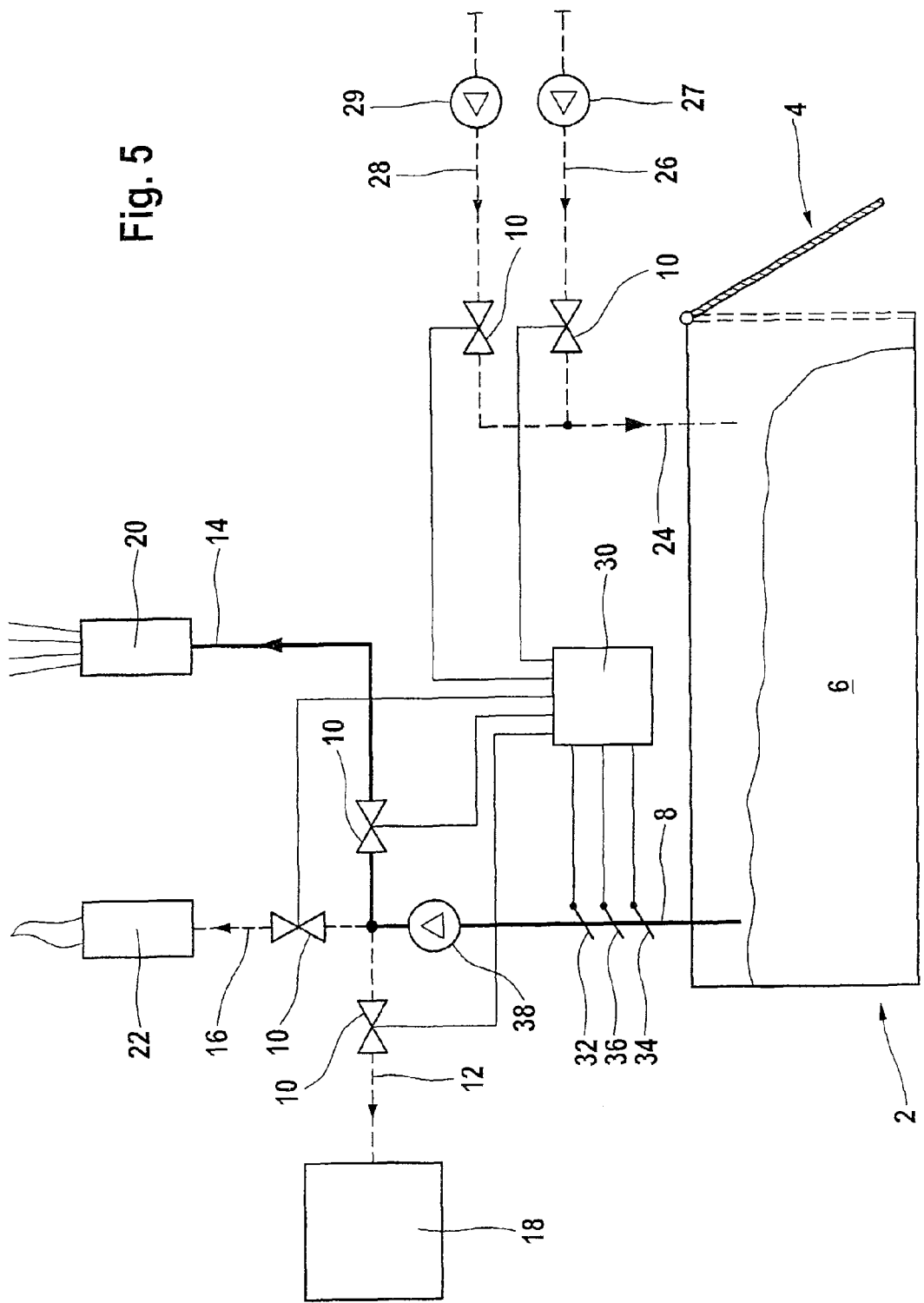

When the carbon dioxide concentration detected by the second measurement sensor 34 in the biogas outlet 8 has dropped below a first limit, the fermenter is switched over to an aerobic process management, so that the fermented biomass present in the still-closed fermenter is composted. At the end of composting, the valve 10 in the fresh air line 28 is closed by the control means 30 and the loading and unloading opening 4 is opened, as is illustrated in FIG. 5.

Figure 6:
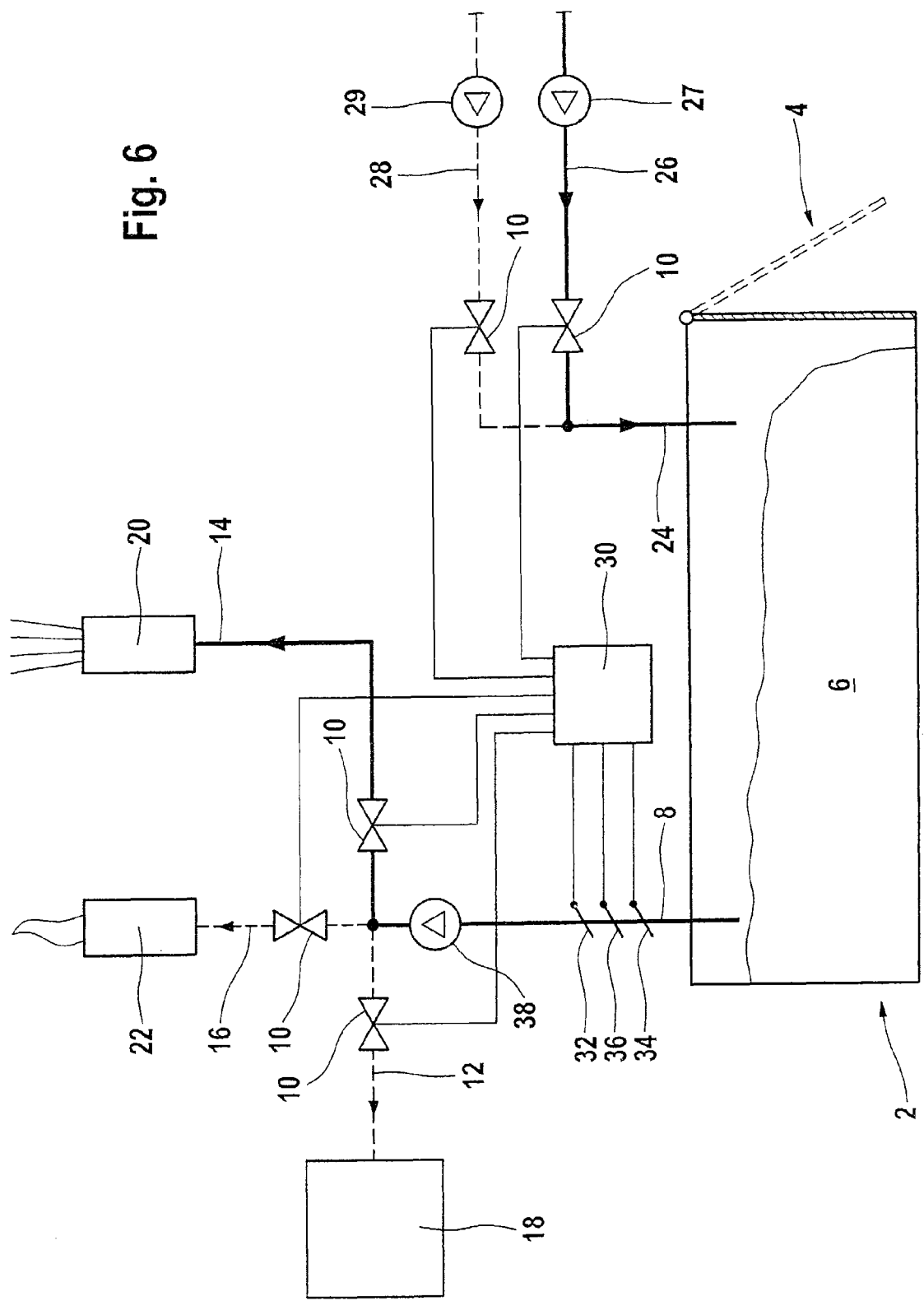

Once the fermenter 2 has been again charged with fresh biomass, the loading and unloading opening 4 is closed, the connection between biogas outlet 8 and waste gas chimney 20 via the first biogas/waste gas line 14 is maintained, and the control means 30 opens the valve 10 in the waste gas line 26, so that waste gas containing carbon dioxide is pumped into the fermenter 2—see FIG. 6. This is continued until the carbon dioxide concentration in the biogas outlet 8 as detected by the second measurement sensor 34 reaches or exceeds a second limit.

Figure 7:
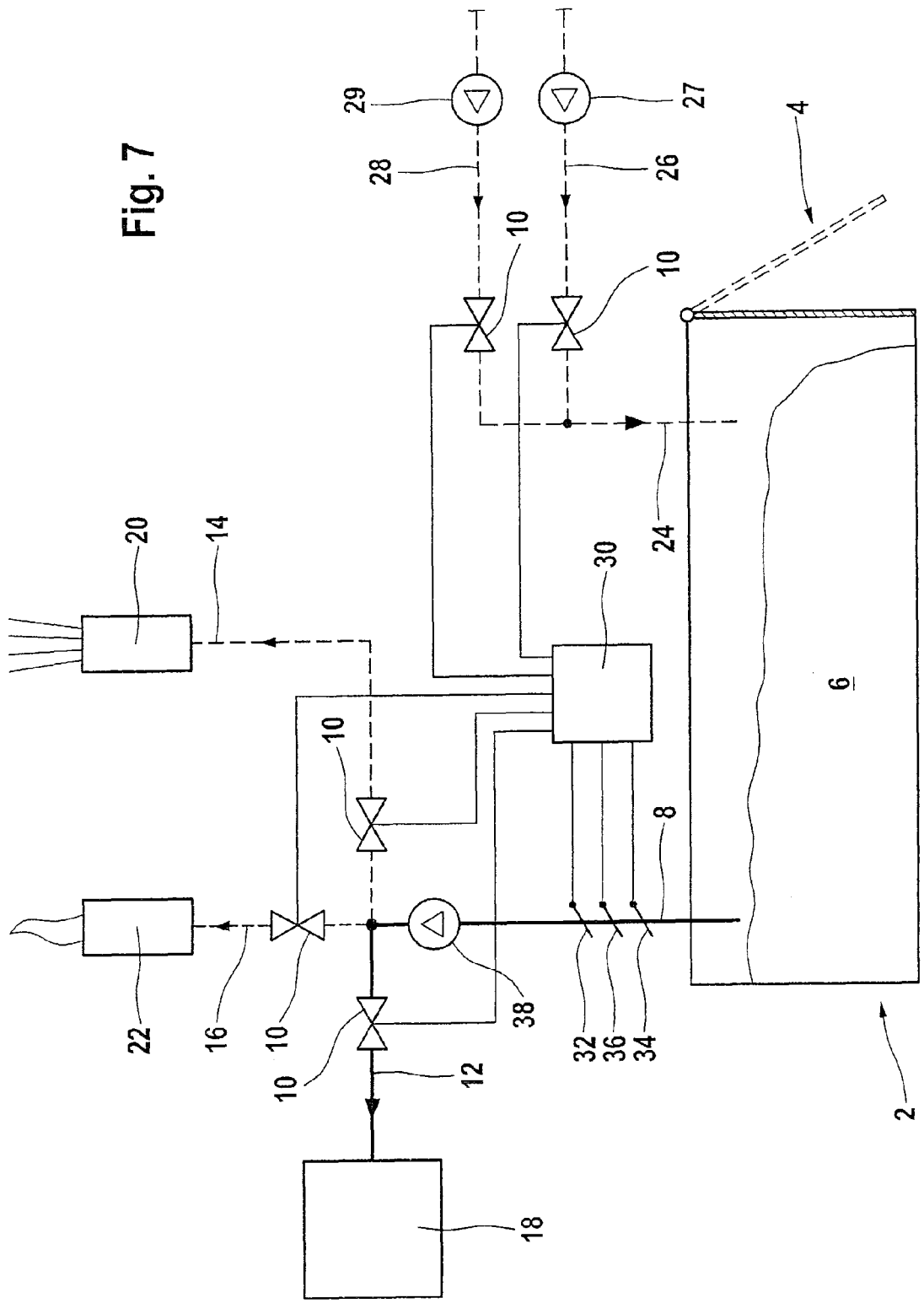

When this second limit for the carbon dioxide concentration has been reached, the control means 30 closes the valve 10 in the waste gas line 26 and in the first biogas/waste gas line 14 and opens the valve 10 in the biogas line 12, as is illustrated in FIG. 7. The biogas production phase has thus been reached again, and the biogas produced in the fermenter 2 is supplied to the block-type thermal power station 18 via the biogas line 12.

Figure 8:
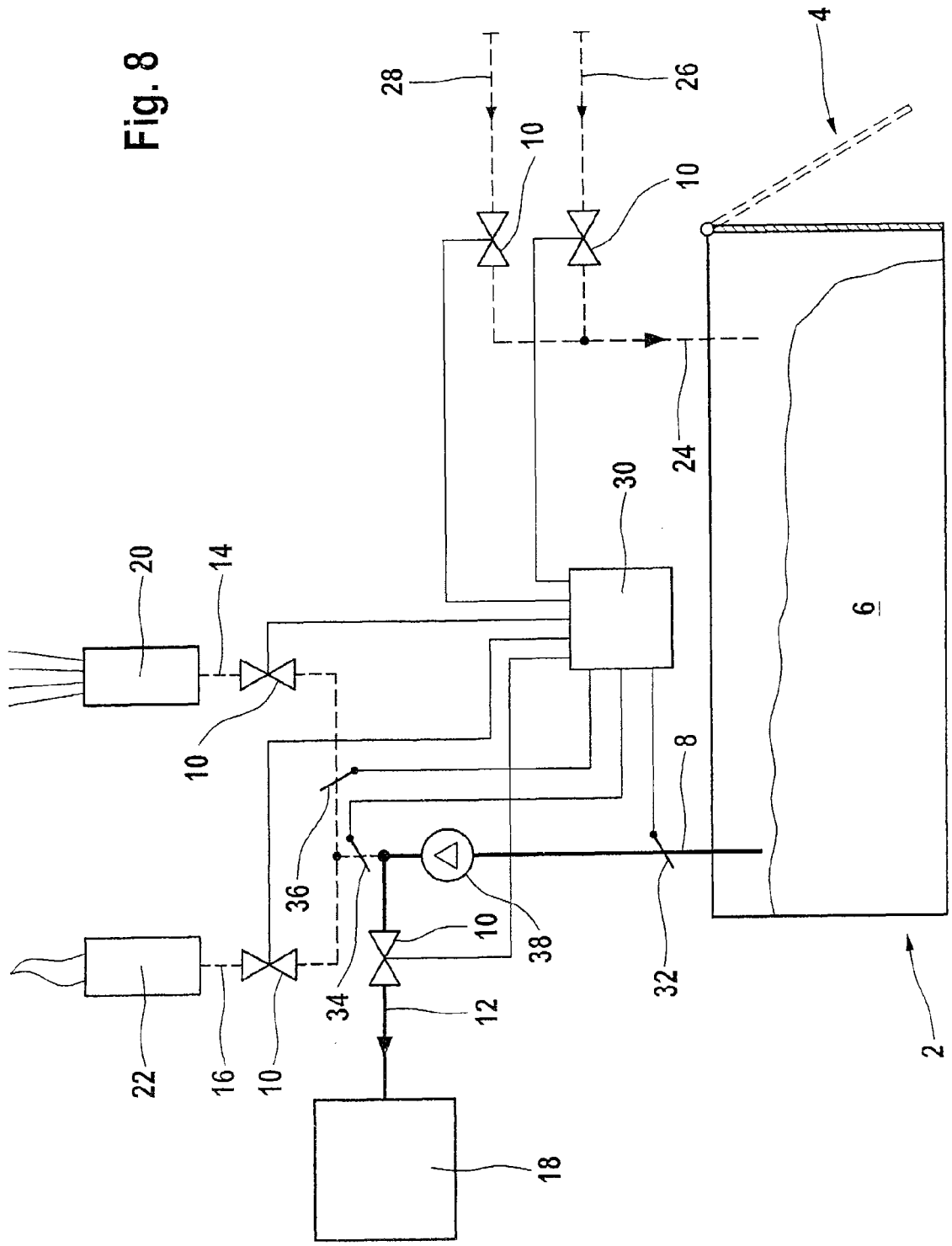
FIG. 8 shows a schematic illustration of a second embodiment of the invention including a fermenter.

In the embodiment described above, all of the measurement sensors 32, 34, 36 are arranged in the biogas outlet 8. According to a second embodiment of the present invention, the second and third measurement sensors 24, 36 may alternatively also be arranged in the first and second biogas/waste gas line 14,16, respectively. FIG. 8 shows an alternative aspect of the invention which differs from the embodiment shown in FIGS. 1 to 7 in that the first and second biogas/waste gas lines 14,16 are combined to form a common biogas/waste gas line 40 before they open into the biogas outlet 8. The second measurement sensor for detection of the carbon dioxide concentration is arranged in the common biogas/waste gas line 40, and the third measurement sensor 36 is arranged in the first biogas/waste gas line 14. For the rest, this second embodiment of the invention corresponds to the first embodiment. The operation is also identical.

FIGS. 9 to 15 show a third embodiment of a combined installation according to the present invention, in which three fermenters 2-1, 2-2 and 2-3 (in the following collectively designated as "2-$i$") are provided in parallel operation. Mutually corresponding components are provided with the same reference symbols. In the combined installation shown in FIGS. 9 to 15, each of the three fermenters 2-$i$ is provided with a purging gas inlet 24-1, 24-2 and 24-3, respectively, each of which may be shut off by a valve 10. The three purging gas inlets 24-$i$ are combined to form a common purging gas inlet 42. A waste gas line 26 and a fresh air line 28, each of which may be shut off by a valve 10, open into the common purging gas inlet 42.

The three fermenters 2-$i$ are each provided with a respective biogas outlet 8-1 8-2 and 8-3 that are each adapted to be shut off by a respective valve 10. The first biogas/waste gas line 14 to the waste gas chimney 20 and the second biogas/waste gas line 16 to the waste gas flare 22 are combined to form a common biogas/waste gas line 40 having a fan 38 arranged in it. Downstream from the fan 38, the common biogas/waste gas line 40 splits into first, second and third biogas/waste gas line elements 40-1, 40-2 and 40-3. The first biogas/waste gas line element 40-1 opens into the first biogas outlet 8-1 between the valve 10 and the first fermenter 2-1. The second biogas/waste gas line element 40-2 opens into the second biogas outlet 8-2 between the valve 10 and the second fermenter 2-2. The third biogas/waste gas line element 40-3 opens into the third biogas outlet 8-3 between the valve 10 and the third fermenter 2-3. The three biogas/waste gas line elements 40-1, 40-2 and 40-3 may each be shut off by a respective valve 10. The three biogas outlets 8-1, 8-2 and 8-3 open into a common biogas line 12 which leads to a block-type thermal power station 18. An exhaust line 44 from the block-type thermal power station 18 opens into a second waste gas chimney 46. The waste gas line 26 is connected via a 3-way valve 48 to the exhaust line 44, i.e., the waste gas containing carbon dioxide which occurs in the block-type thermal power station 18 is used to purge a fermenter 2-$i$ whose fermenting process is to be terminated and which is to be switched over to the composting process. The 3-way valve allows to regulate the volume flow of the waste gas which is sent via the waste gas line 26 for purging a fermenter 2-$i$, as well as the amount of waste gas which is emitted to the environment via the second waste gas chimney 46.

A first measurement sensor 32 for detection of the methane concentration is arranged in the common biogas line 12. A second measurement sensor 34 for detection of the carbon dioxide concentration, a third measurement sensor 36 for detection of the volume flow, and a fourth measurement sensor 50 for detection of the methane concentration are arranged in the common biogas/waste gas line 40, downstream from the fan 38 in the flow direction. The four measurement sensors 32, 34, 36, and 50 are connected to a control means 30. The various valves 10 are likewise connected to the control means. These control lines are not shown in FIGS. 9 to 15 for reasons of clarity.

FIGS. 9 to 15 illustrate termination of the fermentation process inside the fermenter 2-2 and restarting of the second fermenter 2-2 after the composting process which immediately follows the fermentation process and is initiated by switching over the fermenter 2-2, with FIGS. 9 to 15 representing the same phases and operating states as FIGS. 1 to 7. The biogas production of the first and third fermenters 2-1 and 2-3, respectively, takes place continuously during termination of the fermentation process and of the composting process in the second fermenter 2-2 and during restarting of the second fermenter 2-2.

Figure 9:
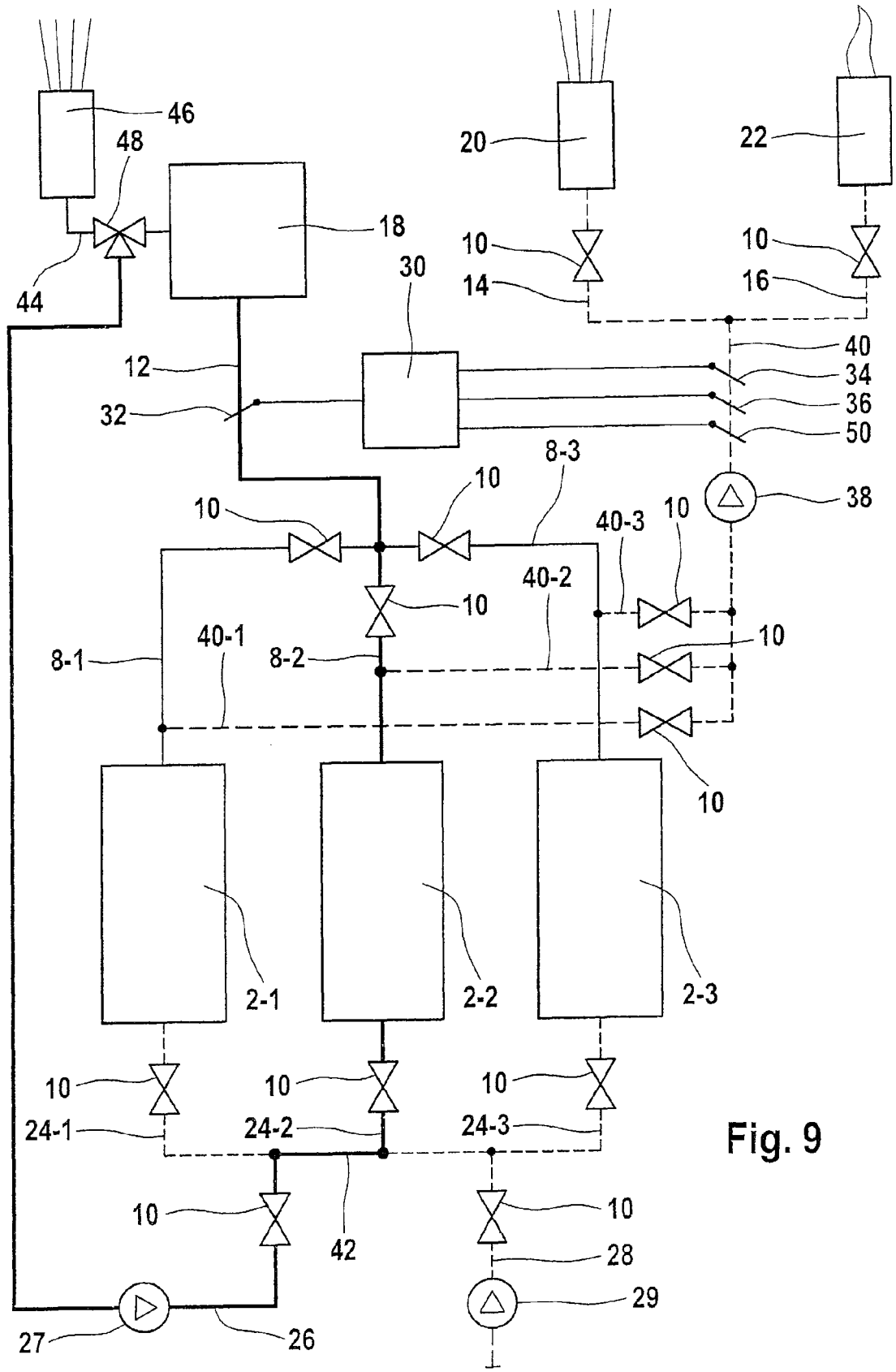
FIGS. 9 to 15 show schematic representations of various operating states of a combined installation including three fermenters during termination of the fermentation process in a fermenter of a combined installation and during (re-)starting of a fermenter.

FIG. 9 shows the first phase of termination of the fermentation process inside the fermenter 2-2, in which phase waste gas containing carbon dioxide from the block-type thermal power station 18 is pumped into the interior of the fermenter 2-2 via the 3-way valve 48 and the waste gas line 26, the waste gas fan 27 and the second purging gas inlet 24-2. As before, the second biogas outlet 8-2 is connected to the common biogas line 12, so that the biogas/waste gas mixture continues to be supplied to the gas processing installation 44.

Figure 10:
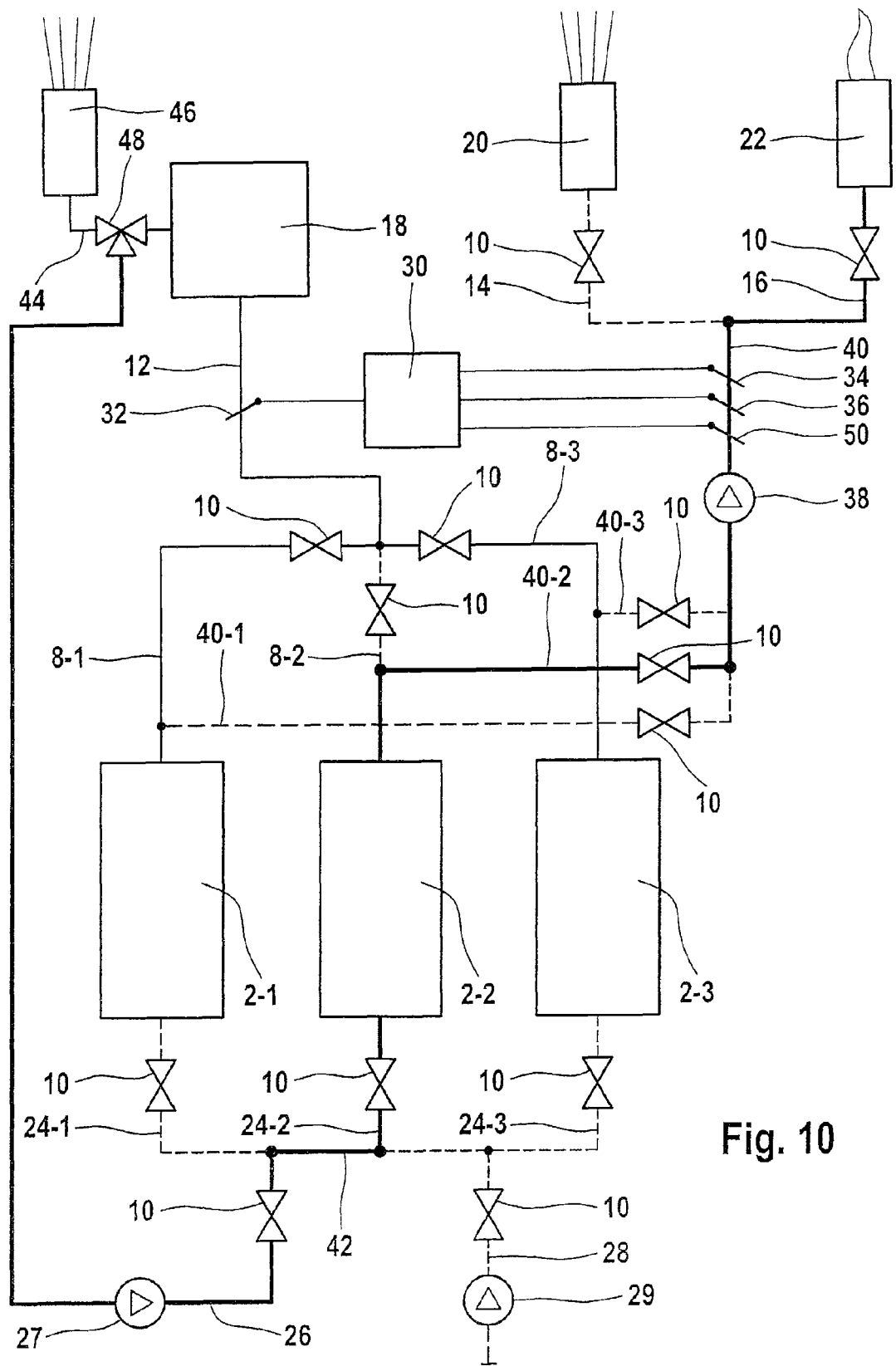

Only when the methane concentration detected by the first measurement sensor 32 in the common biogas line 12 has dropped below an upper limit, the control means 30 closes the valve 10 in the second biogas outlet 8-2 and opens the valve 10 in the second biogas/waste gas line element 40-2 and in the second biogas/waste gas line 16 in a second phase, as is illustrated in FIG. 10. In this second phase of terminating the fermentation process inside the fermenter 2-2, the biogas/waste gas mixture is burnt in the waste gas flare 22. Optionally this combustion process can be assisted by adding additional fuel.

Figure 11:
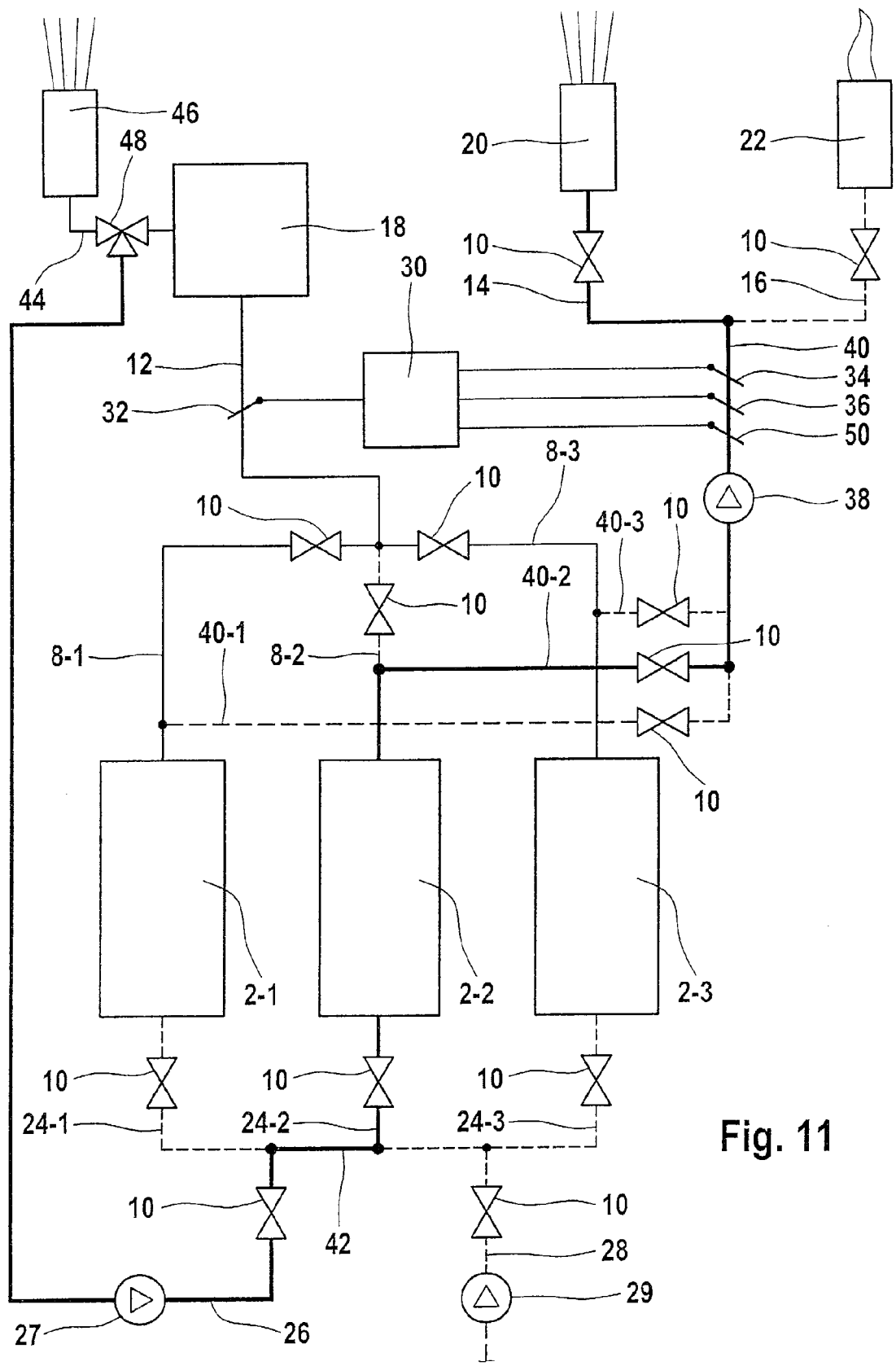

When the methane concentration detected by the fourth measurement sensor 50 in the common biogas/waste gas line 40 has dropped below a medium limit, the control means 30 closes the valve 10 in the second biogas/waste gas line 16 and opens the valve 10 in the first biogas/waste gas line 14 in a third phase, as is illustrated in FIG. 11. In this third phase of terminating the fermentation process inside the fermenter 2-2, the biogas/waste gas mixture is emitted to the environment via the waste gas chimney 20.

Figure 12:
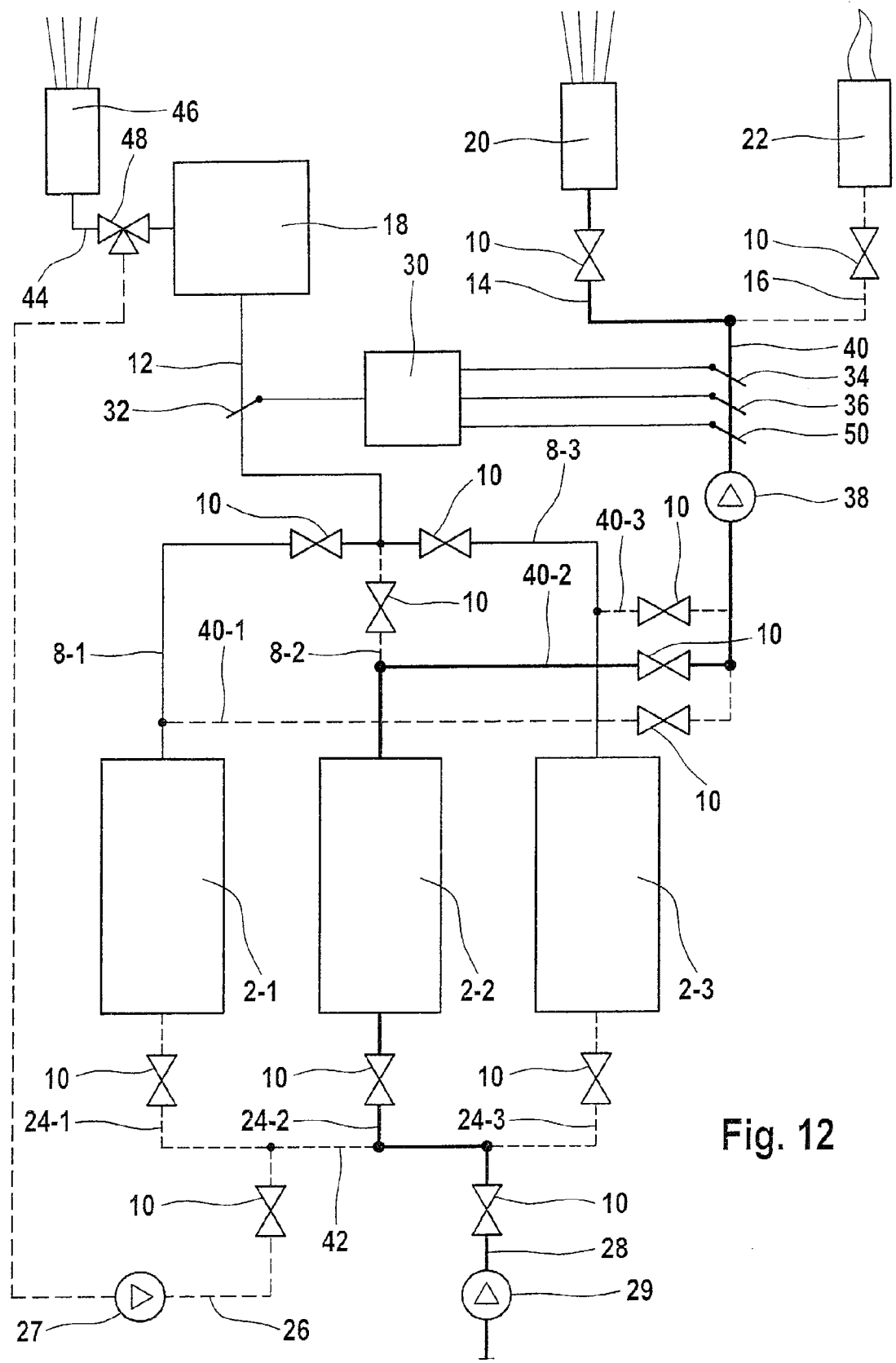
Figure 13:
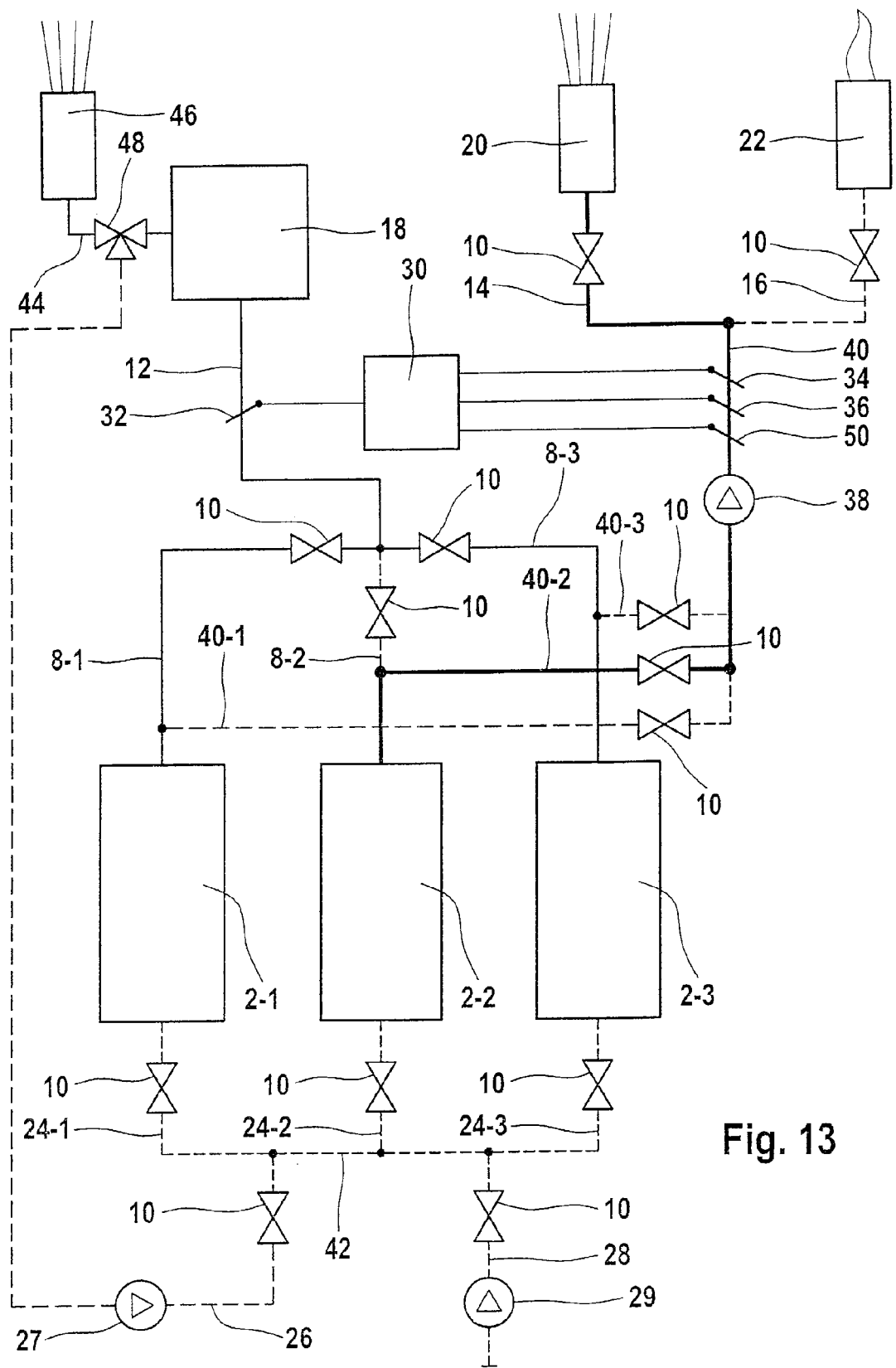

When the methane concentration detected by the fourth measurement sensor 50 in the common biogas/waste gas line 40 has dropped below a lower limit, the control means 30 closes the valve 10 in the waste gas line 26, appropriately switches the 3-way valve 48, and opens the valve 10 in the fresh air line 28 in a fourth phase, as is illustrated in FIG. 12. In this fourth phase of terminating the fermentation process inside the fermenter 2-2, fresh air is pumped into the fermenter 2-2 by the fresh air fan 29 via the fresh air line 28 and the purging gas inlet 24. The waste gas/air mixture continues to be emitted to the environment via the second biogas outlet 8-2, the second biogas/waste gas line element 40-2, the common biogas/waste gas line 40, and the first biogas/waste gas line 14 in the waste gas chimney 20. Optionally this can be assisted by the fan 38.

When the carbon dioxide concentration detected by the second measurement sensor 34 in the common biogas line 40 has dropped below a first limit, the fermenter 2-2 is switched over to initiate composting, and the valve 10 in the fresh air line 28 is closed by the control means 30. Following termination of composting it is possible to open the fermenter 2-2, remove the spent biomass, and charge fresh biomass.

Figure 14:
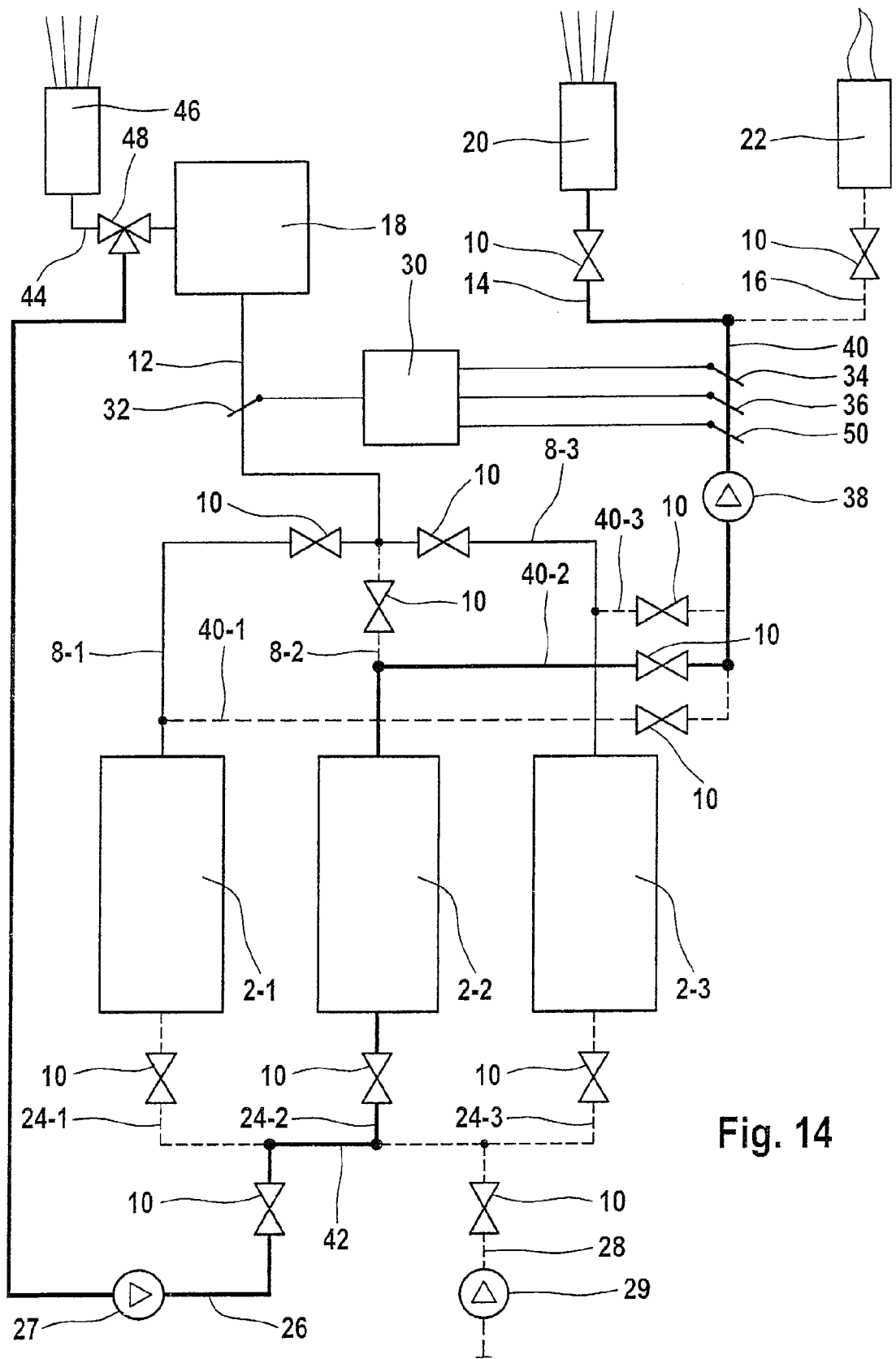

Once the fermenter 2-2 has been recharged with fresh biomass, the loading and unloading opening is closed, the connection between the second biogas outlet 8-2 and the waste gas chimney 20 via the second biogas/waste gas line element 40-2, the common biogas/waste gas line, and the first biogas/waste gas line 14 is maintained, and the control means 30 opens the valve 10 in the waste gas line 26 and switches the 3-way valve 48 in the exhaust line 44 of the block-type thermal power station 18, so that waste gas containing carbon dioxide is pumped into the fermenter 2-2—see FIG. 14. This process continues until the carbon dioxide concentration detected by the second measurement sensor 34 in the common biogas/waste gas line 40 has reached or exceeded a second limit.

Figure 15:
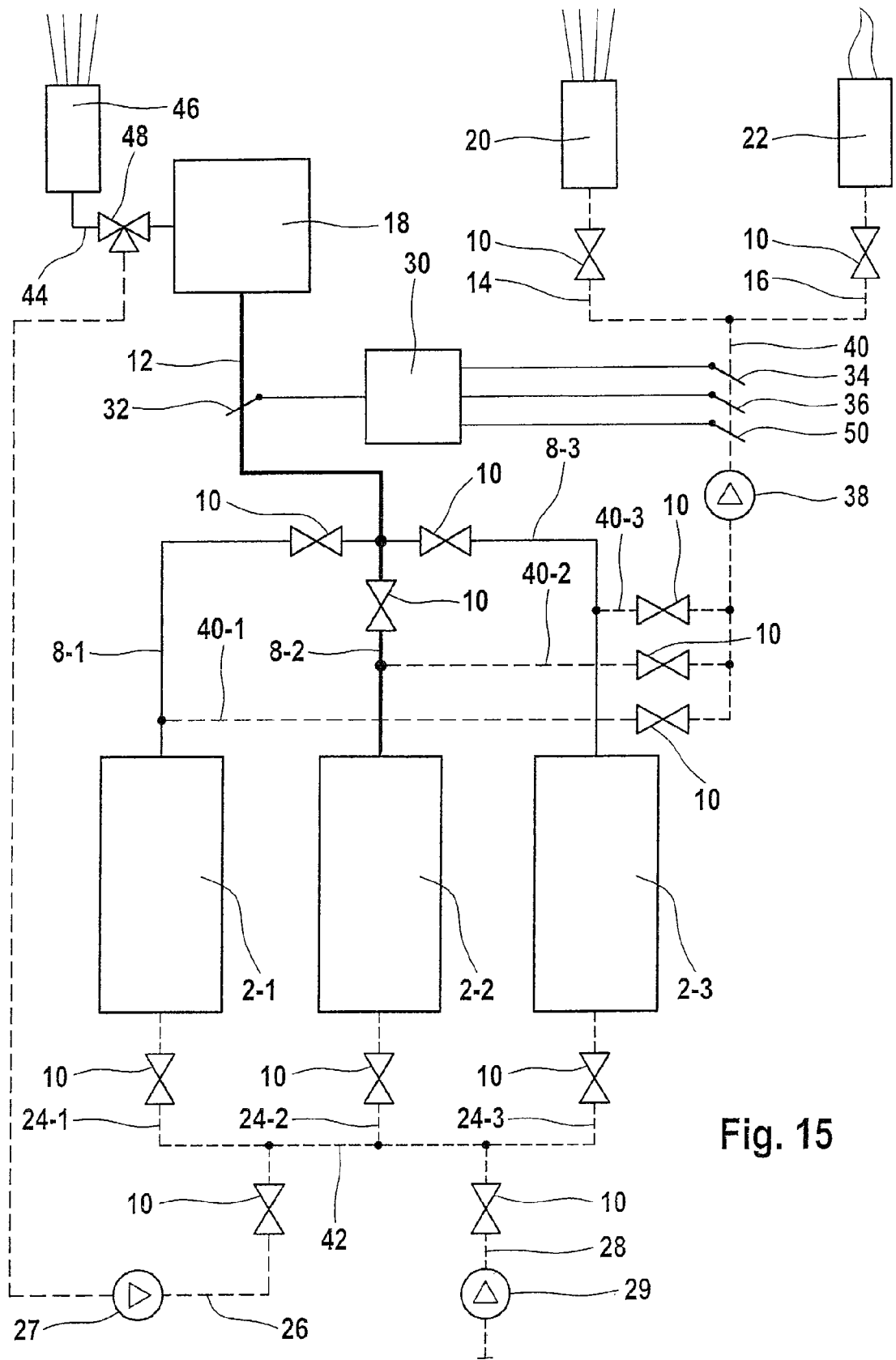

When this second limit for the carbon dioxide concentration has been reached, the control means 30 closes the valve 10 in the waste gas line 26, switches the 3-way valve 38, closes the valve 10 in the second biogas/waste gas line element 40-2, and opens the valve 10 in the second biogas outlet 8-2, as is illustrated in FIG. 15. Thus the second fermenter 2-2 has also once again reached the phase of biogas production, and the biogas produced in the fermenter 2-2 is supplied to the block-type thermal power station 18 via the biogas line 12 of the gas processing installation 44. The biogas outlet 8-2 is not connected to the common biogas line 12 until the methane concentration detected by the fourth measurement sensor 50 has reached a fourth limit. This fourth limit coincides with the upper limit.

The valve 10 in the waste gas line 26 may be omitted since its function can also be carried out by the 3-way valve 48.

In the following, exemplary numerical values for the various limits are given:

| Methane concentration: | upper limit | 30% to 50% |
|---|---|---|
| | medium limit | 10% to 20% |
| | lower limit | 0% to 3% |
| | fourth limit | 30% to 50% |
| Carbon dioxide concentration: | first limit | 0.5% to 2% |
| | second limit | 5% to 15% |

The waste gas volume flow in the waste gas line 26 is between 150 and 1000 m$^3$/h, depending on the size of the fermenters and the amount of waste gas available. The fresh air volume flow in the fresh air line 28 is between 1000 and 5000 m$^3$/h.

Figure 16:
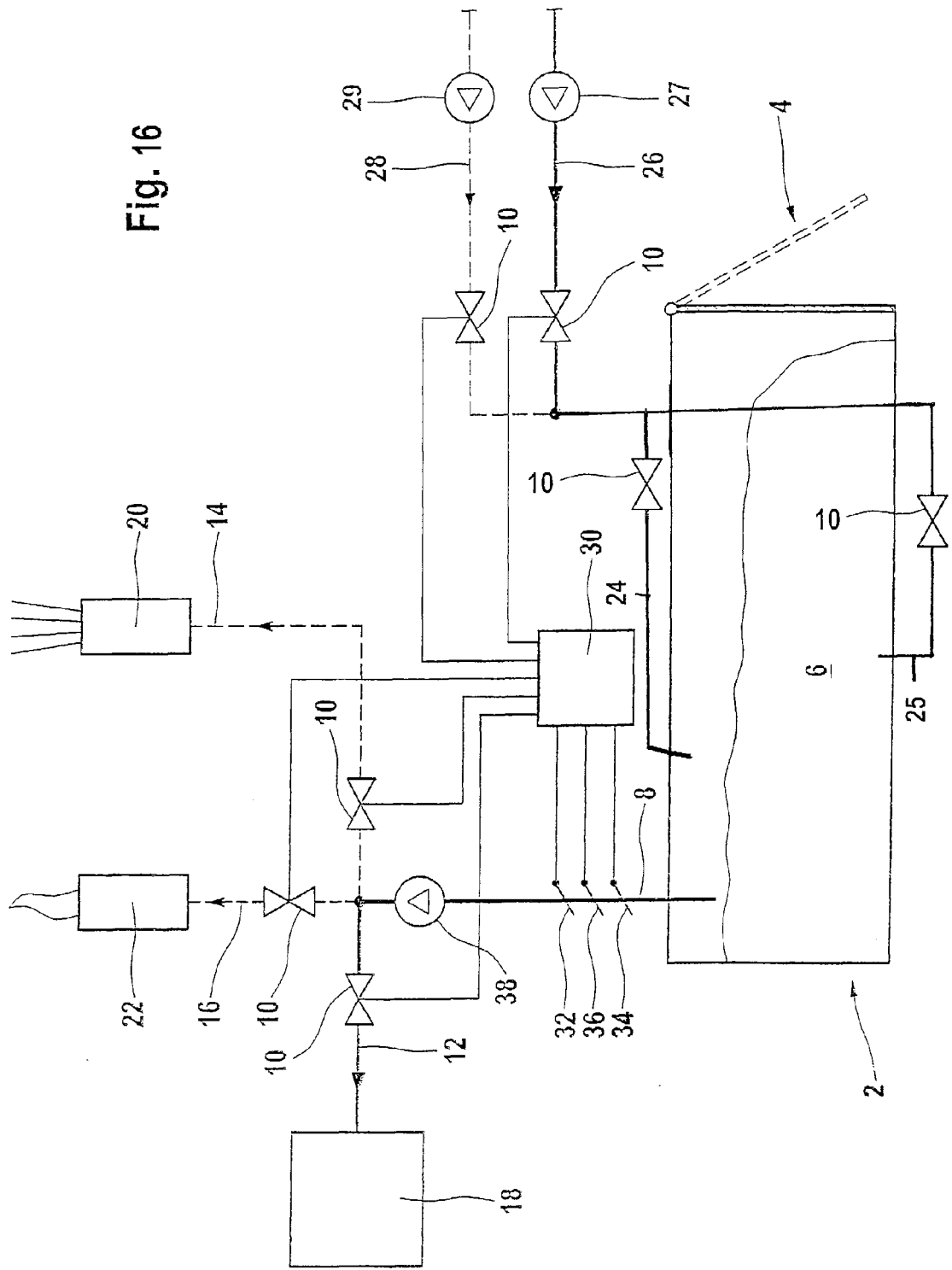
FIG. 16 is a representation corresponding to FIG. 1 of a third embodiment of the invention including a waste gas and fresh air supply, respectively, from the floor plate of the fermenter.

FIG. 16 shows a representation corresponding to FIG. 1 of a combined installation according to a fourth embodiment, which differs from the first embodiment according to FIGS. 1 to 7 in that the purging gas having the form of waste gas or fresh air is supplied in the various operating states not only via the first purging gas inlet 24 in the area above the biomass 6, but additionally or alternatively via a second purging gas inlet 25 in the area of the floor plate of the fermenter 2. This has the effect that biogas present inside the biomass 6 is also "purged out" securely. Moreover this has the effect that the methane slip during loading and unloading of the fermenter is reduced further.

Figure 17A:
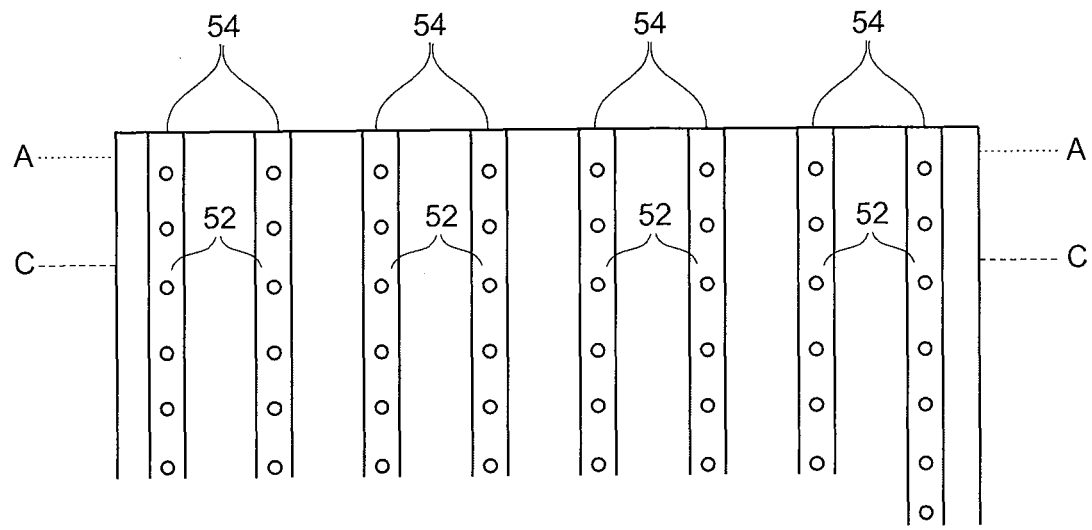
FIG. 17A is a top view of the floor plate having purging gas passages of the fermenter in accordance with the embodiment of FIG. 16.
Figure 17B:
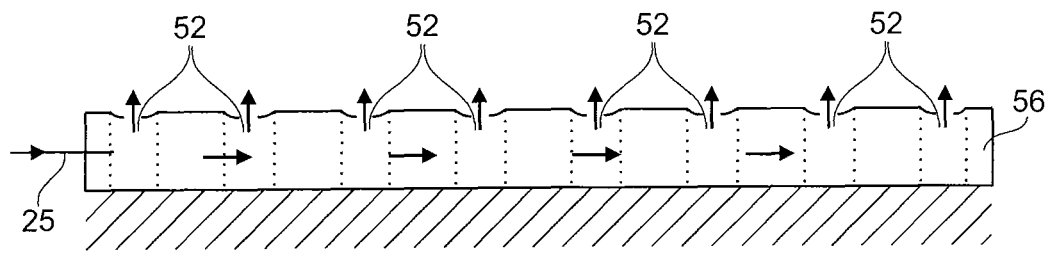
FIG. 17B is a sectional view along line B-B of FIG. 17A with transverse passage and the purging gas passages.
Figure 17C:
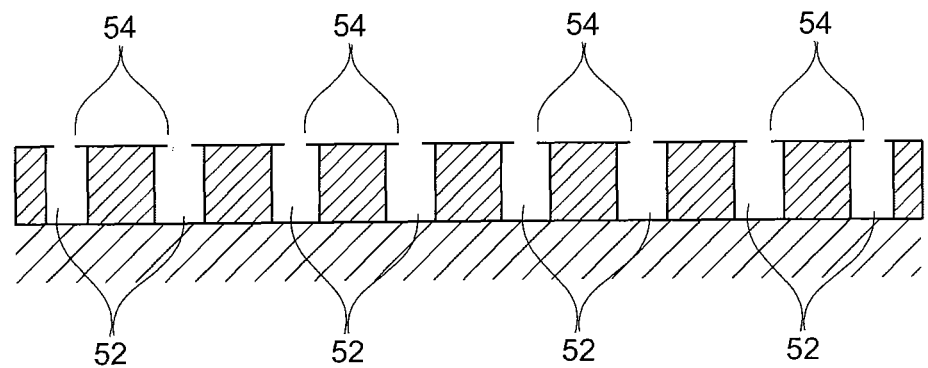
FIG. 17C is a sectional view along line C-C of FIG. 17A with the purging gas passages.

FIG. 17A shows a top view of the floor plate of the fermenter 2 in the embodiment according to FIG. 16. Purging gas passages 52 covered by a liquid- and gas-permeable grid 54 are provided in the floor plate of the fermenter 2 in a longitudinal direction. The various purging gas passages 52 that extend in parallel are interconnected in one ore several locations by a transverse passage 56 extending transversely to the longitudinal direction of the purging gas passages 52. The second purging gas inlet 25 opens into this transverse passage 56. FIG. 17B shows a sectional view along line B-B of FIG. 17A with transverse passage 56 and purging gas passages 52. FIG. 17C shows a sectional view along line C-C of FIG. 17A with purging gas passages 52.

In the embodiments of the invention according to FIGS. 8 and 9 to 15, the supply of purging gas may also be effected via purging gas passages 52 in the floor of the fermenter 2. In the various embodiments the loading and unloading opening is provided on the left-hand side of the fermenter 2. The loading and unloading opening may also be provided on the opposite side.

The invention claimed is:

1. A combined installation for the production of biogas during a fermentation process and for the production of compost during a composting process, the combined installation comprising:
   at least one fermenter operating according to the principle of dry fermentation for the production of biogas in the batch mode and including a biogas outlet and at least one purging gas inlet, the fermenter configured to switch between the fermentation process and the composting process;
   a biogas line connected to the biogas outlet;

a waste gas line whereby waste gas containing carbon dioxide may be supplied to the at least one purging gas inlet;

a waste gas chimney connected to the biogas outlet via a first biogas/waste gas line;

a waste gas flare connected to the biogas outlet via a second biogas/waste gas line;

a fresh air line connected to the at least one purging gas inlet;

a controller for connecting the biogas outlet to the biogas line or to the biogas/waste gas chimney via the first biogas/waste gas line or to the waste gas flare via the second biogas/waste gas line and for connecting the purging gas inlet to the waste gas line or to the fresh air line; and a measurement sensors connected to the controller and including a first measurement sensor for detecting the methane concentration and a second measurement sensor for detecting the carbon dioxide concentration in the gas mixture emerging from the at least one fermenter, wherein the fermenter comprises a floor plate, and in that purging gas passages connected to a second purging gas inlet are provided in the floor plate of the fermenter, and wherein the purging gas passages discharge seepage liquids seeping from a biomass during the production of biogas.

2. Combined installation according to claim 1, characterized in that the measurement sensors are arranged in the biogas outlet.

3. Combined installation according to claim 1, characterized in that a plurality of fermenters are provided, the biogas outlets of which open into a common biogas line, and in that the first measurement sensor for detecting the methane concentration is arranged in the common biogas line.

4. Combined installation according to claim 3, characterized in that the biogas outlets are selectively connected to the waste gas chimney or to the waste gas flare via a common biogas/waste gas line, and in that the second measurement sensor for detecting the carbon dioxide concentration is arranged in the common biogas/waste gas line.

5. Combined installation according to claim 1, characterized in that the waste gas line supplies waste gas from an internal combustion engine.

6. Combined installation according to claim 1, characterized in that the biogas line establishes the connection with a biogas-utiliser producing waste gas that contains carbon dioxide.

7. Combined installation according to claim 6, characterized in that the biogas-utiliser includes a block-type thermal power station.

8. Combined installation according to claim 6, characterized in that the biogas-utiliser includes a fuel cell.

9. Combined installation according to claim 1, characterized in that a first purging gas inlet opens into the fermenter in the area above the biomass.

10. Method of switching a fermenter in a combined installation according to claim 1 between biogas production and composting, including the method steps of:

a) maintaining the connection between biogas outlet and biogas line;

b) connecting the waste gas line to the at least one purging gas inlet of the fermenter to be switched over;

c) purging the fermenter to be switched over with waste gas from the waste gas line until the methane concentration detected by the first measurement sensor has dropped to an upper limit;

d) disconnecting the biogas line from the biogas outlet of the fermenter to be switched over;

e) connecting the biogas outlet of the fermenter to be switched over to the first biogas/waste gas line and supplying the waste gas/biogas mixture to the biogas/waste gas chimney until the methane concentration detected by the first measurement sensor has dropped to a lower limit;

f) disconnecting the waste gas line from the purging gas inlet of the fermenter to be switched over;

g) connecting the fresh air line to the purging gas inlet of the fermenter to be switched over and supplying fresh air into the fermenter to be switched over until the carbon dioxide concentration detected by the second measurement sensor has dropped to a first limit; and h) composting the spent biomass inside the fermenter.

11. Method according to claim 10, characterized in that the following method steps are carried out between method step d) and method step e):

d1) connecting the biogas outlet of the fermenter to be switched over to the second biogas/waste gas line and supplying the waste gas/biogas mixture to the waste gas flare until the methane concentration detected by the first measurement sensor has dropped to a medium limit that is situated between the upper and lower limits; and d2) disconnecting the biogas outlet of the fermenter to be switched over from the second biogas/waste gas line.

12. Method according to claim 10, characterized in that the fresh air supplied via the fresh air line is pre-heated.

13. Method according to claim 10, characterized in that the composting process is controlled by way of the supplied amount of fresh air.

14. Method according to claim 10, characterized in that the gas mixtures discharged from the fermenter are filtered.

15. Method according to claim 10, characterized in that the waste gas line is connected to the exhaust of an internal combustion engine.

16. Method according to claim 10, characterized in that the waste gas line is connected to the exhaust of a biogas processing means that produces waste gas containing carbon dioxide.

17. Method according to claim 10, characterized in that the waste gas line is connected to the exhaust of a fuel cell.

18. Method for starting up a fermenter according to claim 1 that was freshly charged with biomass, including the following method steps:

a) closing the loading and unloading opening;

b) connecting the biogas outlet to the first biogas/waste gas line;

c) connecting the waste gas line to the purging gas inlet of the fermenter to be started up, and supplying waste gas to the fermenter to be started up, until the carbon dioxide concentration detected by the second measurement sensor has reached a second limit;

d) disconnecting the waste gas line from the purging gas inlet;

e) disconnecting the first biogas/waste gas line from the biogas outlet;

f) connecting the biogas line to the biogas outlet.

19. Method according to claim 18, characterized in that method step f) is carried out when the methane concentration detected by the first or fourth measurement sensor exceeds a fourth limit.

20. Method according to claim 19, characterized in that the fourth limit of methane concentration is equal to the upper limit of methane concentration.

* * * * *